United States Patent [19]

Salvo

[11] 4,360,342

[45] Nov. 23, 1982

[54] METHOD FOR REPLACING LOST TEETH

[76] Inventor: Christopher A. Salvo, 656 King St., Port Chester, N.Y. 10573

[21] Appl. No.: 205,986

[22] Filed: Nov. 12, 1980

[51] Int. Cl.³ ............................................. A61C 13/22
[52] U.S. Cl. .................................... 433/172; 433/174; 433/180
[58] Field of Search ............... 433/180, 181, 182, 172, 433/174, 215

[56] References Cited

U.S. PATENT DOCUMENTS

| | | | |
|---|---|---|---|
| 446,769 | 2/1891 | Clowes | 433/180 |
| 715,492 | 12/1902 | Littig | 433/180 |
| 1,340,089 | 5/1920 | Stone | 433/181 |
| 1,649,905 | 11/1927 | Lasky | 433/172 |
| 2,151,723 | 3/1939 | Trinkle | 433/172 |
| 3,348,311 | 10/1967 | Weissman | 433/215 |
| 3,395,455 | 8/1968 | Overby et al. | 433/215 |
| 3,487,545 | 1/1970 | Weissman | 433/215 |
| 3,499,222 | 3/1970 | Linkow et al. | 433/174 |
| 3,641,670 | 2/1972 | Karageorge | 433/180 |
| 3,708,883 | 1/1973 | Flander | 433/174 |
| 3,822,472 | 7/1974 | Garfinkel | 433/215 |

OTHER PUBLICATIONS

"Metal-Reinforced Anterior Tooth Replacement Using Acid-Etch-Composit Resin Technique", Nathanson et al., J. of Pros. Den., pp. 408-412, 4/1980.

Primary Examiner—Gene Mancene
Assistant Examiner—John J. Wilson
Attorney, Agent, or Firm—LeBlanc, Nolan, Shur & Nies

[57] ABSTRACT

A method and apparatus for replacing missing teeth without a massive restoration is disclosed. The dental bridge of this invention includes a flat bar or mesh support which is mounted on one or more abutment teeth. The support carries one or more pontics. The pontic may be mounted on the support when the support is manufactured or by the dentist. The abutment teeth are prepared by removing no more than ½ to 1 millimeter of the occlusal or lingual surface just past the juncture of the enamel and dentin. The support is then fitted in the preparation and mounted with screws or pins located to miss the vital nerve and pulpal structure. The bridge is then covered with a conventional filling.

6 Claims, 12 Drawing Figures

METHOD FOR REPLACING LOST TEETH

This invention relates to dental bridges, and to an improved dental bridge which may be easily and relatively quickly fitted into the patient's mouth without a massive restoration or removal of significant portions of abutment teeth. The bridge of this invention is intended to be mass produced and can be easily adapted to replacing one or more teeth, whether the teeth are anterior, posterior, or both.

A variety of bridge structures have been in use for many years. For example see U.S. Pat. Nos. 1,649,905 and 2,151,723. Dental bridge structures are characterized by the removal of substantial portions of abutment teeth to provide a mounting seat for screws or pins. The tooth portion then must be capped or restored. The operation then involves significant patient discomfort and normally will be a lengthy procedure which can be quite expensive.

Accordingly, there is a need for a relatively inexpensive permanent bridge which may be mass produced and which may be installed without removing massive portions of abutment teeth.

The device of this invention includes a support bar, rod, or mesh plate which may mount one or more pontics. The pontics may be mounted on the support when the support is manufactured or the pontics may be mounted on the support by the dentist. The bridge of this invention is intended to be mounted with only a minimal removal of tooth structure from abutment teeth and attached without the use of an inlay, crown, cap or any prosthesis. The bridge of this invention is attached directly to abutment teeth by use of small pins or screws. The bridge of this invention is intended to be fitted in a preparation ½ to 1 millimeter deep so that the bridge will be secured against movement by both the screws or pins and by its location within the preparation.

The bridge of this invention is intended to be used to replace either anterior teeth or posterior teeth, or both. The pontic may be manufactured from any material, and after the bridge is attached to the tooth structure, it is covered with a filling so that the entire procedure involves minimal patient discomfort.

Accordingly, it is an object of this invention to provide a dental bridge device which may be mass produced and installed with only a minor removal of tooth structure.

It is another object of this invention to provide a dental bridge which may be mounted directly to abutment teeth and which may mount one or more pontics as desired.

It is another object of this invention to provide a method for replacing missing teeth which involves minimal patient discomfort and is relatively fast and inexpensive.

It is yet another object of this invention to provide a method for mounting a dental bridge which requires removal of mostly enamel portions of abutment teeth in a predetermined configuration so that when the bridge is installed a filling may be used to cover the bridge structure, and a cap, or crown will not be necessary.

These and other objects will become readily apparent with reference to the drawings and following description wherein.

Figures 7A, 7B, 7C:
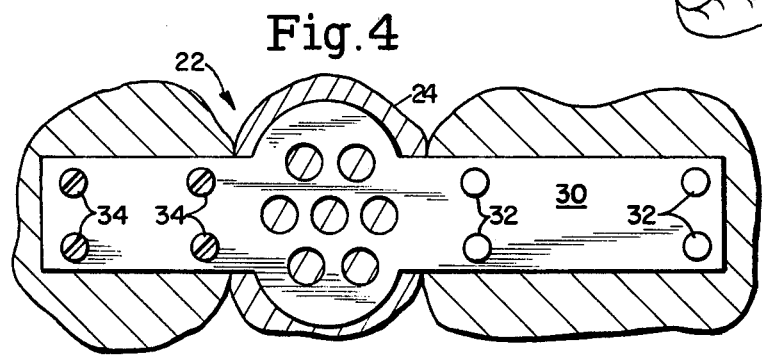

FIGS. 7A, B, and C are side views of two screws and a pin which may be used to secure the support of this invention.

Figures 8A, 8B, 8C:
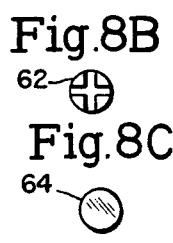

FIGS. 8A, B and C are alternate end views of the screws of FIGS. 7A and B and an end view of the pin of FIG. 7C.

Figure 1:
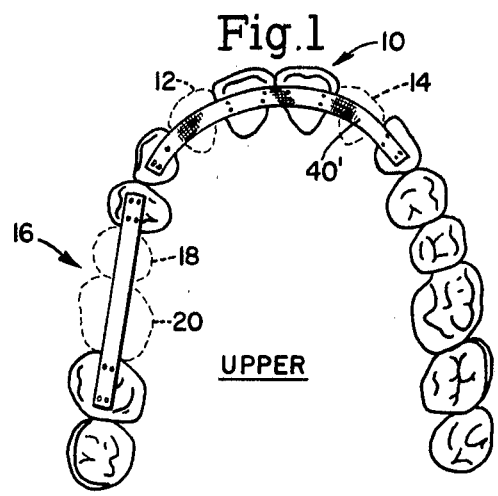
FIG. 1 is a representation of a human tooth structure having the bridge of this invention installed at four locations.
Figure 2:
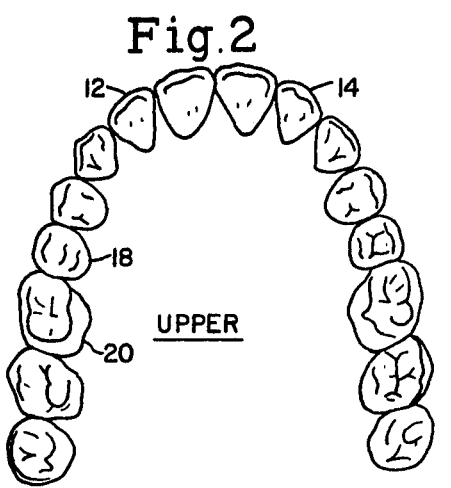
FIG. 2 is a representation similar to FIG. 1 after the bridge installation is complete.

With attention to the drawings, FIG. 1 illustrates different embodiments of the bridge of this invention after preparation and installation of the bridges but before the final filling step. FIG. 2 is the post-operative appearance of the teeth of FIG. 1. FIG. 2 also conforms to the natural appearance.

With attention to FIG. 1, pontics are shown in phantom. The bridge 10 illustrates an anterior placement of pontics 12 and 14 wherein the bridge is anchored to abutment teeth at either end and at the center. The bridge at 16 illustrates double pontics 18 and 20 with the bridge secured to abutment teeth at either end. The bridge at 22 also mounts a pontic 24 and is secured at either end of abutment teeth. In contrast, the bridge at 26 illustrates a double abutment with the pontic 28 mounted at an end thereof. In the bridge at 10 both marginal ridges are removed from the incisors, and only a single marginal ridge is removed from each of the cuspids. Bridges at 16 and 22 likewise involve removal of a single marginal ridge from the abutment teeth. The bridge at 26, however, entails the removal of both marginal ridges from the second biscuspid.

As shown in FIG. 1 also, the anterior bridge 10 involves a preparation on the lingual side of the front teeth. Bridges 16, 22 and 26, involve preparations on the occlusal surface of posterior teeth.

Figure 3:
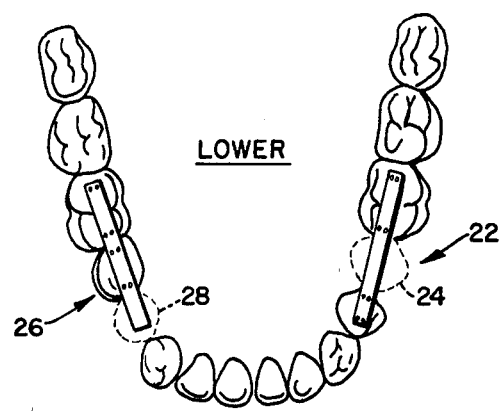
FIG. 3 is a cross-sectional view illustrating installation of the bridge of this invention.

With attention to FIGS. 3 and 4, to illustrate the bridge of this invention relative to posterior teeth, the bridge comprises a horizontal support member 30 which may be a bar, a rod, or mesh as will be subsequently explained. The support member is foraminous with a plurality of holes 32 formed therein. Holes 32 are intended to receive small screws or pins 34 for securing the bridge to abutment teeth. The screws or pins are properly located so as to miss entering vital nerve or pulpal structures shown generally at 36 in FIG. 3.

In the case of posterior teeth the occlusal surface structure is prepared 1 millimeter to ½ millimeter apically or dentin in the configuration of the support member 30. Enamel is removed just past the junction of enamel and dentin, and the purpose of this removal is to hold the support member 30 against lateral movement. The screws or pins 34 are then located in the tooth structure of the abutment teeth to miss entering vital nerve and pulpal structures and to thereby hold the support member 30 in place with firmness so that no movement thereof either vertically or hozontially is permitted. If desired, the support member 30 may be initially cemented in place with any conventional dental adhesive or embedded on filling material before it is attached to the abutment teeth by pins 34.

The pontic 24 may be attached to the support member 30 be being formed around a projection 31 as well as around perforations in 30 at pontic 24. The pontic may be of porcelain or any other conventional material such as acrylic, polycarbonate, or metal. After the support member 30 is secured as shown in FIG. 4, filling material is used to cover all of the infrastructure or attaching structure of the bridge of this inventon. The result is the tooth structure of FIG. 2.

Figure 5:
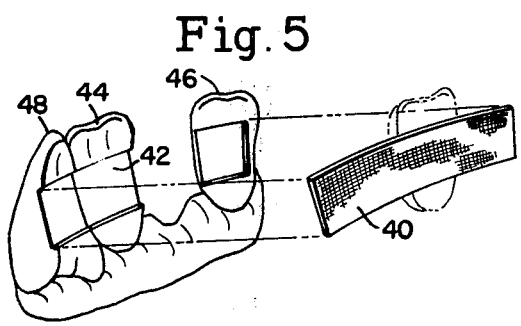
FIG. 5 is an exploded view of anterior teeth and a bridge of this invention.
Figure 6:
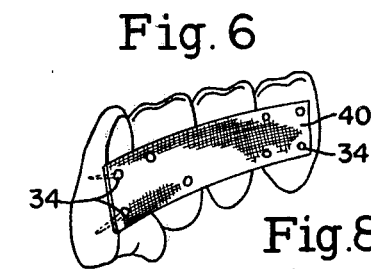
FIG. 6 is a view similar to FIG. 5 showing installation of the bridge of this invention prior to filling.

With reference to FIGS. 5 and 6, in the case of anterior teeth a mesh support 40 is preferred. In contrast, with posterior teeth such as shown in FIGS. 3 and 4, a bar or rod or flat type plate support 30 is preferred. The mesh connector 40 is easier to conform to the dental arch as shown, whereas the flat bar or rod support is more suitable for flat occlusal surfaces, and provides greater strength and ease of manipulation. Because of the acute curvature of the dental arch, however, mesh support 40 will be more suitable for one or two pontics. As shown in FIG. 1, bridge 10, comprises a mesh support 40'.

With attention to FIG. 5, the initial preparation involves removal of from 1 to ½ millimeter into dentin from abutment teeth in the configuration of support 40. The preparation 42 may involve removal of both marginal ridges from a tooth 44, but the most distant marginal ridge from edentulous area remains intact. In FIG. 5, the most distant marginal ridges of teeth 46 and 48 then remains intact.

After the preparation of the abutment teeth, the tap holes are drilled into the dentinal structure and the mesh positioned in the lingual preparation. The pins or screws 34 are then inserted through the mesh into the tap holes. If desired, the mesh may be cemented in place before drilling the tap holes with a suitable cement. Once the mesh is fitted and secured any desired filling material may be used to seal the mesh work and screws in the tooth.

As noted above, the pontics may be preformed on the support member. If a preformed pontic is used, after the preparation of abutment teeth an accurate impression of the abutment and edentulous ridge is taken. The impression is then cast in a fast (impression plaster) setting, or a slower setting (stone) plaster to serve as a working model. The gingival relation of the pontic face to the gingiva is made on the model using a suitable grinding wheel or wheels and where the pontic is porcelain, a glaze of low fusing porcelain is placed over the roughened area before placing in the mouth. As will be obvious to thosed skilled in the art, usual polishing procedures are employed when plastic materials are chosen.

This invention also comprises a preparation of a bridge without a preformed pontic whereby the pontic is formed and processed about the support member by the dentist. Usual procedures obvious to those skilled in the art would be utilized to form the pontic.

Figure 4:
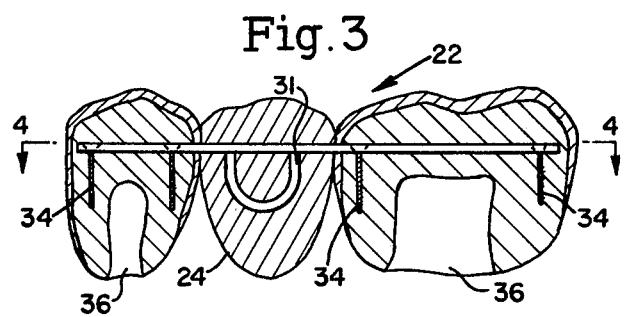
FIG. 4 is a view taken along line 4—4 of FIG. 3

As shown in FIGS. 4 and 6, the support member is foraminous so that appropriate screw holes may be selected to give maximum support to the bridge and to miss vital healthy pulpal tissues. A larger screw (not shown) could also be designed to enter a non-vital root and should have the proper length, diameter and taper to match without stress so that it may be used to secure the support member after a proper root canal treatment has been completed.

Anterior and posterior teeth may be joined where desired by either the mesh or bar support member depending upon which can be bent to fit the ½ to 1 millimeter preparation in the dentino-enamel junction. The junction preparation as noted above is intended to receive the support member as snuggly as possible to prevent lateral movement thereof. As will be obvious to those skilled in the art, excess pressures which might cause splitting of the tooth structure should be avoided.

With attention to FIGS. 7A and B and FIGS. 8A and B the support member of this invention may be secured with tiny screws 34. Typically the screws may have a flat head 60 or a beveled head 62. The head itself may have a single driver-receiving slot as shown in FIG. 8A, or it may be a Phillips head as shown in FIG. 8B.

Pins 32 also are alternatively contemplated to secure the support of this invention to the tooth structure. Pins 32 may have a flat head 64 as shown in FIG. 8C. In addition the shank 66 may be provided with a plurality of barbs 68 to retain the pin 32 in the tooth structure.

Typically heads 60, 62, and 64 are about ¼ to ½ millimeter thick and about 1.25 millimeters in diameter. Screw 34 and pin 32 are about 5 millimeters in length and typically about 0.020, 0.025, or 0.030 in diameter. Screw 34 may have 90 to 100 threads per inch.

In summary then, the dental bridge of this invention provides a means for replacing missing teeth without elaborate preparations and with a minimum of patient discomfort. The bridge involves a preparation only up to about 1 millimeter in depth in the dentinal configuration of a support member. One or more pontics are formed on the support member, and the support is affixed in the preparation by screws or pins. The support may be cemented in addition if desired. It is preferred to use a flat bar or rod support for posterior teeth and a mesh support for anterior teeth. The support in anterior teeth would be affixed to the lingual surface and therefore must be bent to conform to the dental arch. The support in the case of posterior teeth is affixed to the occlusal surface and therefore would be flat. Pins or screws are intended to be inserted in the tooth structure to miss pulpal tissue, and subsequently the entire preparation is covered with conventional filling material so that the end result will be identical to the natural appearance. This invention is not intended to be limited to the type of pontic or filling material utilized and comprehends the use of any conventional material. It is preferred, however, that the pontic be of porcelain. The support and/or the pins and screws may be of stainless steel or a chrome-cobalt alloy or other known materials including non metals such as nylon. The choice of materials will be obvious to those skilled in the art.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and equivalency of the claims are therefore intended to be embraced therein.

What is claimed and desired to be secured by Letters Patent is:

1. A method for replacing lost teeth without removal of substantial portions of abutment teeth whereby a bridge may be permanently fixed in a patient's mouth comprising: providing a support having a plurality of holes therethrough, and a predetermined shape and configuration said support having at least one pontic mounted thereon at a predetermined location; removing a portion from the adjacent teeth conforming to the shape of said support and from about 0.5 to about 1 millimeter deep to just below the enamel-dentin junction to form a support receiving preparation with resistance and retention form for holding the support against lateral movement to resist dislodgement and retain the support in the preparation; drilling holes at predetermined locations in said adjacent teeth; mounting said support and pontic on said adjacent teeth in said preparation and fixing said support thereto with pins on screws through the holes therein and into the holes drilled in the tooth structure; and covering said support with a dental filling.

2. The method of claim 1 further comprising providing a metal mesh support.

3. The method of claim 2 wherein said bridge is intended to replace at least one anterior tooth and said preparation is formed by removal of the lingual surface of a plurality of abutment teeth conforming to the shape of said support and in a configuration corresponding to the patient's dental arch.

4. The method of claim 1 further comprising providing an elongated rod or plate support.

5. The method of claim 4 wherein said bridge is intended to replace at least one posterior tooth and said preparation is formed by removal of the occlusal surfaces of a plurality of abutment teeth, apically, conforming to the shape of said support.

6. The method of claim 1 wherein the step of fixing said support in said preparation includes the step of applying an adhesive to said preparation before seating said support therein.

* * * * *